(12) United States Patent
Hancock et al.

(10) Patent No.: US 11,344,367 B2
(45) Date of Patent: May 31, 2022

(54) ELECTROSURGICAL APPARATUS AND ELECTROSURGICAL INSTRUMENT

(71) Applicant: CREO MEDICAL LIMITED, Chepstow (GB)

(72) Inventors: Christopher Paul Hancock, Bath Bath and North East Somerset (GB); Patrick Burn, Chepstow (GB); Malcolm White, Chepstow (GB); Louis Turner, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 370 days.

(21) Appl. No.: 16/472,181

(22) PCT Filed: Feb. 7, 2018

(86) PCT No.: PCT/EP2018/053097
§ 371 (c)(1),
(2) Date: Jun. 20, 2019

(87) PCT Pub. No.: WO2018/146159
PCT Pub. Date: Aug. 16, 2018

(65) Prior Publication Data
US 2020/0022755 A1    Jan. 23, 2020

(30) Foreign Application Priority Data

Feb. 10, 2017    (GB) ...................... 1702252

(51) Int. Cl.
*A61B 18/18*    (2006.01)
*A61B 18/00*    (2006.01)
(52) U.S. Cl.
CPC ............... *A61B 18/1815* (2013.01); *A61B 2018/00541* (2013.01); *A61B 2018/00577* (2013.01);
(Continued)

(58) Field of Classification Search
CPC ...... A61B 18/1815; A61B 2018/00541; A61B 2018/00577; A61B 2018/00732;
(Continued)

(56) References Cited

U.S. PATENT DOCUMENTS 5,298,682 A    3/1994    Salz
6,287,302 B1    9/2001    Berube
(Continued)

FOREIGN PATENT DOCUMENTS

EP         2085978 A2      8/2009
GB         2545179 A       6/2017
WO    WO 2009/039093 A2    3/2009

OTHER PUBLICATIONS

British Search Report cited in British Application No. GB1702252.6 dated Jun. 20, 2017.
(Continued)

*Primary Examiner* — Kaitlyn E Smith
(74) *Attorney, Agent, or Firm* — ArentFox Schiff LLP

(57) ABSTRACT

An electrosurgical instrument capable of supporting resonance of microwave energy at multiple frequencies. The instrument comprises a coaxial cable and a radiating distal tip portion arranged to receive microwave energy from the coaxial cable. The radiating tip portion consists of a dielectric material having an electrical length selected in conjunction with its dielectric properties at three or more frequencies of microwave energy to support resonance at each frequency. By providing a single device that can effectively couple microwave energy into biological tissue at three or more frequencies, tissue ablation can be performed rapidly with accuracy. The instrument may be used in an apparatus that includes a generator arranged to supply microwave energy at three or more different frequencies.

22 Claims, 6 Drawing Sheets

(52) U.S. Cl.
CPC ............ *A61B 2018/00732* (2013.01); *A61B 2018/00785* (2013.01); *A61B 2018/1823* (2013.01); *A61B 2018/1876* (2013.01)

(58) Field of Classification Search
CPC .. A61B 2018/00785; A61B 2018/1823; A61B 2018/1876; A61B 2018/00916; A61B 2018/00077; A61B 2018/00107; A61B 2018/1273; A61B 2018/128; A61B 2018/00994
USPC ........................................................ 607/101
See application file for complete search history.

(56) References Cited

U.S. PATENT DOCUMENTS

| | | | | |
|---|---|---|---|---|
| 7,831,298 B1* | 11/2010 | Wang | ................ | A61B 18/1815 600/473 |
| 2011/0034917 A1* | 2/2011 | Brannan | ................ | A61B 18/00 606/41 |
| 2011/0125148 A1* | 5/2011 | Turner | ............... | A61B 18/1815 606/33 |
| 2011/0208179 A1* | 8/2011 | Prakash | ............. | A61B 18/1477 606/33 |
| 2011/0213352 A1 | 9/2011 | Lee et al. | | |
| 2012/0172865 A1* | 7/2012 | Hancock | ............ | H01Q 21/0075 606/33 |
| 2013/0165915 A1* | 6/2013 | Thiel | ...................... | A61B 90/57 606/33 |
| 2014/0290830 A1 | 10/2014 | Brannan | | |
| 2014/0378958 A1 | 12/2014 | Leussler | | |
| 2015/0196353 A1* | 7/2015 | Hancock | ............ | A61B 18/1815 606/46 |
| 2015/0272673 A1 | 10/2015 | Cronin et al. | | |
| 2015/0351836 A1* | 12/2015 | Prutchi | ............. | A61B 18/1492 606/41 |
| 2016/0135887 A1* | 5/2016 | Prakash | ................. | A61B 18/18 606/33 |
| 2019/0069951 A1* | 3/2019 | Hancock | ............ | A61B 18/1492 |

OTHER PUBLICATIONS

International Search Report and Written Opinion cited in International Application No. PCT/EP2018/053097 dated Jun. 7, 2018.

* cited by examiner

ELECTROSURGICAL APPARATUS AND ELECTROSURGICAL INSTRUMENT

CROSS-REFERENCE TO RELATED APPLICATIONS

This application is a National Stage entry of International Application No.: PCT/EP2018/053097, filed Feb. 7, 2018, which claims priority to Great Britain Patent Application No. 1702252.6, filed Feb. 10, 2017. The disclosures of the priority applications are hereby incorporated in their entirety by reference.

TECHNICAL FIELD

The present application relates to an electrosurgical apparatus for delivering electromagnetic (EM) energy into biological tissue at multiple frequencies. In particular, the application relates to an electrosurgical instrument for non-invasive or percutaneous insertion to a treatment site, which is configured for efficient delivery of EM energy to tissue at multiple microwave frequencies.

BACKGROUND TO THE INVENTION

Electrosurgical devices and apparatus for supplying EM energy to body tissue are known.

Typically, apparatus for delivering EM energy to body tissue comprises a generator comprising a source of EM energy, and an electrosurgical instrument connected to the generator, for delivering the energy to tissue.

EM energy, and in particular microwave and radio-frequency (RF) energy, have been found to be useful in electrosurgical operations, for their ability to cut, coagulate, and ablate body tissue.

Furthermore, it is known to use microwave emitting probes to treat various conditions in the lungs. For example, microwave radiation can be used to treat asthma and ablate tumours or lesions in the lungs.

SUMMARY OF THE INVENTION

At its most general, the present invention provides an electrosurgical instrument capable of supporting resonance of microwave electromagnetic (EM) energy at multiple frequencies, e.g. three or more frequencies greater than 1 GHz. By providing a single device that can effectively couple microwave energy into biological tissue at three or more frequencies, tissue ablation can be performed rapidly with accuracy.

According to the invention, there may be provided an electrosurgical instrument for delivering microwave electromagnetic (EM) energy into biological tissue, the instrument comprising: a coaxial cable for conveying microwave EM energy, the coaxial cable having an inner conductor, an outer conductor, and a first dielectric material separating the inner conductor and the outer conductor; and a radiating tip portion disposed at a distal end of the coaxial cable to receive microwave EM energy from the coaxial cable, the radiating tip portion comprising a second dielectric material different from the first dielectric material, wherein the radiating tip portion has an electrical length selected in conjunction with its dielectric properties at three or more frequencies of microwave EM energy to support resonance at the three or more frequencies of microwave EM energy. The invention operates using the principle that different frequencies of microwave EM energy penetrate into biological tissue to different depths, and in particular that higher frequencies of EM energy result in faster and more localised heating of body tissue. Conventional tissue ablation techniques tend to use frequencies that heat a larger volume of body tissue, but take a longer period of time to produce a desired temperature increase. Thus there appears a necessary trade-off between size of ablation and speed of treatment.

The normal mechanism by which energy is transferred into biological tissue at microwave frequencies (i.e. greater than 1 GHz) is dielectric heating, where the microwave EM energy drives molecular oscillations in the tissue. Typically, biological tissue adjacent to the dielectric heating zone also experiences a rise in temperature. The mechanism for this is conduction, i.e. heat energy dissipating from the dielectric heating zone. The inventors have observed that a combination of these two heating mechanisms at a plurality of frequencies can enable microwave EM energy to create a rise in temperature of a larger treatment zone than is typically associated with microwave energy frequencies. Moreover, heating in this zone can be achieved in a shorter time frame than is possible if lower (non-microwave) EM energy is used.

The treatment technique of the invention uses a plurality of frequencies in part to adapt to changes in physical and dielectric properties of biological tissue caused by heating. In particular, changes in dielectric properties can affect a relative impedance match between the radiating tip portion, the coaxial cable, and the tissue. The efficiency of energy delivery to biological tissue at lower frequencies can be improved by first heating the tissue at a higher frequency.

Herein, references to microwave EM energy mean electromagnetic energy having a frequency greater than 1 GHz, e.g. in a range between 1 GHz and 300 GHz. Preferred frequencies are 2.45 GHz, 5.8 GHz and 14.5 GHz, since they are known to produce particularly desirable heating effects for ablating tumours, especially lung tumours. These three frequencies in combination can provide heating effects that are effective in the treatment of haemorrhoids and/or fistulas, and so it is envisioned that the present invention can further be used to treat haemorrhoids and fistulas.

The frequencies at which the radiating tip portion supports resonance may not be limited to the three frequencies discussed above. For example, the radiating tip portion may support resonance at four frequencies. Preferably, the radiating tip portion may support resonance at five frequencies. More preferably, the radiating tip portion may support resonance at six frequencies.

Advantageously, the radiating rip portion may further support delivery of energy at other frequencies, e.g. 433 MHz and/or 915 MHz. These frequencies are also known to be particularly effective for ablating lung tumours, and for treating haemorrhoids and/or fistulas.

It is known to use radiofrequency (RF) EM energy to heat tissue by resistive heating to produce desired therapeutic effects. Hence, in some embodiments, the electrosurgical instrument may further be arranged to deliver RF EM energy, e.g. having a frequency between 3 kHz and 300 MHz. To assist with the delivery of RF energy to tissue, the distal-most point of the inner conductor may extend past a distal-most point of the second dielectric material, e.g. so that the distal-most point of the radiating tip portion comprises an exposed portion of the inner conductor. Advantageously, the radiating tip portion may further support delivery of energy at a frequency of 400 kHz. This frequency is also known to be particularly effective for ablating lung tumours, and for treating haemorrhoids and/or fistulas.

It is noted that the distal end of the coaxial cable is defined, for the purposes of this application, as being distal from a notional generator supplying the EM energy to the coaxial cable, i.e. distal from an end of the coaxial cable that is configured to receive EM energy from a generator.

For the purposes of the present application, resonance is defined as a situation in which the magnitude of power reflected at the radiating tip portion (i.e. reflected power $S_{1,1}$ as measured at a proximal end of the coaxial cable) is −10 dB, or better. Preferably, the power reflected at the radiating tip portion is −12 dB, or better. More preferably, the power reflected at the radiating tip portion is −15 dB, or better.

By providing a distal radiating tip portion capable of supporting resonance at multiple frequencies, energy is effectively delivered into the tissue.

Resonance occurs when the length of a cavity in which a wave oscillates is approximately equal to a half-integer multiple of the wavelength of the wave, thereby enabling a standing wave to exist, with a displacement node at each end of the cavity. Hence, by having a second dielectric material at the radiating tip portion that is different from the first dielectric material of the coaxial cable, the interface between the first dielectric and the second dielectric provides a well-defined boundary at which a displacement node can exist, such that the second dielectric material can be considered as a cavity in which resonance may be supported. Accordingly, it is possible to choose the frequencies at which the radiating tip portion resonates, by selecting a physical length L of the second dielectric material that substantially satisfies $$L = \frac{n\lambda}{2},$$

where n is a positive integer, and λ is a wavelength of microwave EM energy that propagates in the second dielectric material at one of the three of more frequencies of microwave EM energy. Selecting an appropriate length of the second dielectric material, i.e. so that it satisfies this expression at each of the three or more frequencies may not be trivial. This is because the wavelength (λ) of the EM energy in the radiating tip portion is itself dependent on a number of factors, including: frequency of the energy, frequency-dependent magnetic permeability of the radiating tip portion, frequency-dependent dielectric permittivity of the radiating tip portion, geometry of the radiating tip portion, and the material into which the tip is inserted.

The second dielectric material may have a length approximately equal to half of the wavelength (i.e. n=1) in the second dielectric material at 2.45 GHz, approximately equal to one wavelength (i.e. n=2) in the second dielectric material at 5.8 GHz, and approximately equal to 2.5 wavelengths (i.e. n=5) in the second dielectric material at 14.5 GHz.

In practice, the length of the second dielectric material may have a length that differs from the length defined in the equation above by up to 10%. Preferably, the length only differs from the length defined above by up to 5%.

The second dielectric material may comprise an elongate probe extending distally away from the coaxial cable, the elongate probe having a cylindrical shape with a diameter equal to or less than a diameter of the coaxial cable.

The second dielectric material may have a lower impedance than the first dielectric material at each of the three or more frequencies of microwave EM energy. Moreover, the second dielectric material may have an impedance that lies between the impedance of the cable (typically 50Ω), and an impedance of the tissue into which the tip is inserted (typically much lower than 50Ω for body tissue). The radiating tip portion may then have a geometry selected so that it acts as an impedance transformer, as well as supporting resonance, in order to promote delivery of energy into tissue. In particular, the radiating tip portion may form an impedance transformer in the radial direction (i.e. the direction extending radially away from the inner conductor).

The second dielectric material may be a ceramic dielectric material, e.g. that exhibits low loss at the three or more microwave frequencies. Preferably, it may be made from Macor® ceramic. By providing a (rigid) ceramic material, the instrument may be particularly well-suited to percutaneous insertion into the body (i.e. insertion to the human body through an incision). Macor® ceramic is particularly desirable because it has a low impedance; and is non-porous and chemically inert (making it biocompatible).

By contrast, the first dielectric material may be PTFE. When the first and second dielectric materials are respectively PTFE and Macor® ceramic, the radiating tip portion forms an effective impedance transformer, due to the low impedance value of Macor® ceramic relative to PTFE. Delivery of the EM energy to tissue is thereby further improved.

The distal end of the radiating tip portion may be tapered to a point, so as to assist with percutaneous access to body tissue. Preferably, it may taper to a sharp point. Having a sharp/tapered end further helps with percutaneous insertion into the body.

Alternatively, the coaxial cable and radiating tip portion may be dimensioned so as to enable non-percutaneous access to body tissue, e.g. through a natural orifice in the body of a patient. In embodiments in which the instrument is used non-percutaneously, the distal end of the radiating tip portion may be rounded, i.e. to prevent piercing an airway or other natural passageway in the body down which the instrument is to be passed.

The coaxial cable and radiating tip portion may be configured to be insertable down an instrument channel of a bronchoscope or endoscope. In particular, the coaxial cable will preferably be flexible in such embodiments, to assist with insertion e.g. into an airway.

The outer conductor may extend beyond a distal end of the first dielectric material to enclose a proximal portion of the second dielectric material. This can influence the shape of the emitted field. Hence, ablation pattern can be controlled by simply changing the frequency of energy delivered to the instrument, i.e. using a generator capable of supplying energy to the instrument at multiple frequencies, according to a selectable energy delivery profile.

The inner conductor of the coaxial cable may extend beyond a distal-most point the outer conductor, beyond a distal-most point of the first dielectric material, and towards a distal-most point of the radiating portion. Moreover, the inner conductor may extend into the second dielectric material, and toward a distal-most end of the dielectric material. A radiating tip portion having this structure radiates as a dipole antenna, thereby promoting radiation of energy radially away from the radiating tip portion for deep ablation.

The distal-most points of the first dielectric material, of the outer conductor, and of the radiating tip portion, are defined in the same way as the distal end of the coaxial cable, i.e. relative to a notional generator supplying the EM energy to the instrument.

Preferably, the inner conductor does not extend beyond the distal-most point of the second dielectric material, and is not exposed anywhere along the radiating tip portion.

The outer diameter of the radiating tip portion may be substantially equal to the outer diameter of the coaxial cable. The portion of the second dielectric material that is encased by the outer conductor may in fact have an outer diameter that is equal to the inner diameter of the outer conductor, e.g. for ease of manufacture and for a good seal to prevent ingress of fluids into the end of the instrument.

The outer conductor may encase the second dielectric material for at least half of the length of the second dielectric material. Preferably, the outer conductor may encase the second dielectric for up to three-quarters of its length. By having the second dielectric material encased in this way, a field shaping effect is produced, such that the ablation pattern/shape produced by the radiating tip portion is concentrated towards a distal end of the radiating tip portion at higher frequencies.

The inventors have also found that the portion of the radiating tip portion for which the second dielectric material is encased by the outer conductor acts as an impedance transformer between the coaxial cable and the distal end of the radiating tip portion, thereby further improving delivery of the EM energy into tissue.

In some embodiments, the coaxial cable may have a hollow lumen passing through it, i.e. travelling parallel to the longitudinal axis of the coaxial cable. Such a hollow lumen may be used for delivering and/or removing fluid from a space surrounding the radiating tip portion.

In another aspect, there is provided an electrosurgical apparatus for delivering microwave electromagnetic (EM) energy into biological tissue, the apparatus comprising: a generator arranged to generate microwave EM energy at three or more different frequencies; and an electrosurgical instrument as set out above, wherein the coaxial cable has a proximal end connected to the generator to receive microwave EM energy therefrom.

The generator may comprise three or more separate microwave sources for generating microwave EM energy at a respective one of the three or more different frequencies. The generator may further comprise a signal combiner arranged to convey each signal to a common signal path that is connected to the coaxial cable. The signal combiner may be a multiplexer. The multiplexer may be operable as a switching unit for selecting a signal to be conveyed on the common signal path. Alternatively or additionally, the multiplexer may be operable to convey two or more of the signals on the common signal path in a simultaneous or quasi-simultaneous manner. For example, the multiplexer may be a time-domain multiplexer or a filter multiplexer.

The apparatus may include a surgical scoping device (e.g. bronchoscope or the like) having flexible instrument cord for non-invasive insertion to a treatment site, wherein the instrument cord includes an instrument channel, and wherein the electrosurgical instrument is dimensioned to be insertable within the instrument channel.

The generator may be operable to deliver microwave EM energy at the three or more different frequencies according to a predetermined energy delivery profile. The energy delivery profile may be selected according to a desired ablation depth, and/or a desired ablation zone shape. In some embodiments, the energy delivery profile may be selected based on a measured property of energy reflected from the radiating tip portion.

In one example, the generator may be operable under the predetermined energy delivery profile to: deliver a first signal during a first ablation period, the first signal comprises microwave EM energy having predominantly a first frequency; deliver a second signal during a second ablation period, the second signal comprises microwave EM energy having predominantly a second frequency, which is less than the first frequency; deliver a third signal during a third ablation period, the third signal comprises microwave EM energy having predominantly a third frequency, which is less than the first frequency and the second frequency. The generator may switch or alternate between the three periods. In particular, the energy may be (rapidly) alternated between the three frequencies. Alternatively, the energy may be supplied at the three frequencies simultaneously.

The second frequency may be less than half the first frequency. The third frequency may be less than half the second frequency. For example, the first frequency is 14.5 GHz, the second frequency is 5.8 GHz, and the third frequency is 2.45 GHz.

By supplying the EM energy using the delivery profiles outlined above, the rapid and localised heating effect at 14.5 GHz can be used to rapidly ablate tissue close to the radiating tip portion. Once this tissue has been suitably ablated, e.g. after the predetermined time has elapsed, the energy at the lower frequencies can then enlarge the ablation zone, taking advantage of an improved dielectric match between the radiating tip portion and the tissue. Hence, the time to heat the larger ablation zone is reduced when compared with the time it would have taken if operating at the first frequency only.

A further advantage of heating according to an alternated profile, is that heating effects in the coaxial cable (which are more pronounced at 14.5 GHz) do not give rise to a significant temperature increase in the coaxial cable, because the periods of time over which energy is supplied at the lower frequencies allow for dissipation of any localised heating effects along the length of the cable.

The generator may be configured to deliver pulses of microwave energy in time with the breathing cycle of a patient. Hence, energy can be supplied when lungs are deflated, in order to provide a better relative impedance match between the coaxial cable, radiating tip portion, and tissue.

The generator may include a detector arranged to detect reflected power received back from the coaxial cable, and wherein the generator is arranged to switch from one ablation period to the next ablation period based on the detected reflected power.

BRIEF DESCRIPTION OF THE DRAWINGS

Examples of the present invention are discussed in detail below with reference to the accompanying drawings, in which.

DETAILED DESCRIPTION; FURTHER OPTIONS AND PREFERENCES

Figure 1:
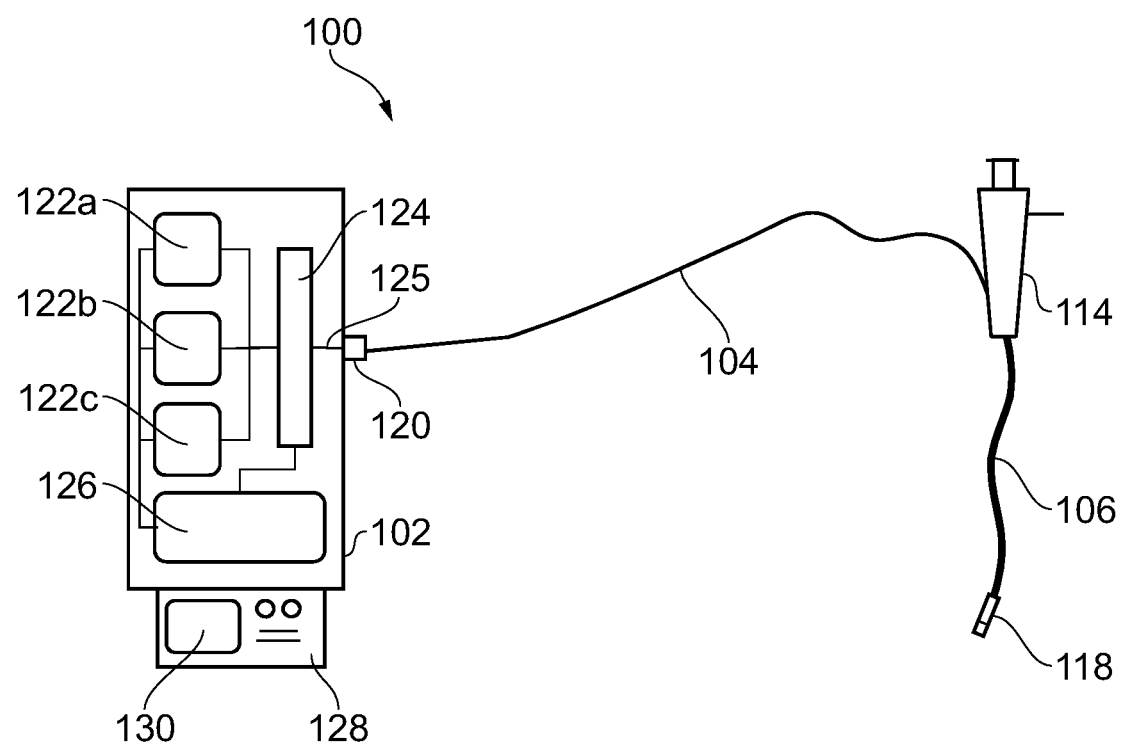
FIG. 1 is a schematic diagram of an electrosurgical apparatus that is an embodiment of the present invention.

FIG. 1 is a schematic diagram of an electrosurgical apparatus 100 that is an embodiment of the invention. The apparatus 100 is operable to selectively supply EM energy having a plurality of frequencies into biological tissue at a treatment site in a localised manner. The apparatus 100 comprises a generator 102 for generating EM energy having a plurality of frequencies. The generator 102 has a output port 120 to which is connected a coaxial cable 104. The coaxial cable 104 conveys the EM energy away from the generator 102 towards an electrosurgical instrument 118. In this embodiment, the coaxial cable 104 is inserted through an instrument channel within an insertion cable 106 of a bronchoscope 114. The insertion cable 106 is a flexible, steerable shaft capable of non-invasive insertion into a patient's lungs. This embodiment therefore enables a non-percutaneous insertion of the instrument 118. However, in other embodiments, the instrument 118 may have a distal tip configured for percutaneous insertion, i.e. for accessing lung tissue through an incision made in the body of a patient. In such an example, the instrument may be inserted directly into the tissue or via a suitable catheter.

The generator 102 comprises three separate microwave sources 122a, 122b, 122c. Each of the separate microwave sources 122a, 122b, 122c generates a signal having a different frequency. In this example, the frequencies are 2.45 GHz, 5.8 GHz and 14.5 GHz. Each of the separate microwave sources 122a, 122b, 122c may include a corresponding power amplifier for amplifying the respective signal to a power level suitable for use.

In some embodiments, the three sources may be integrated into a single component, e.g. a GaN power device. The use of a GaN power device, such as a GaN High Electron Mobility Transistor (HEMT)-based device, can enable the generator set-up to be miniaturised. On the other hand, the use of separate sources may be more cost-effective in some circumstances.

The generator 102 includes a multiplexer 124 connected to receive an output signal from each of the separate microwave sources 122a, 122b, 122c. The multiplexer 124 operates to transfer the separate signals onto a common output path 125, which is connected to the output port 120. The multiplexer 124 may switch between the outputs of the separate microwave sources 122a, 122b, 122c, or may combine two or more of the outputs so that they are transmitted simultaneously. The multiplexer 124 may be operable as both a switch and a signal combiner.

The generator 102 includes a controller 126 operatively connected to the multiplexer 124 and each of the separate microwave sources 122a, 122b, 122c. The controller 126 can control operation of the generator 102 to output a desired signal. As discussed below, a desired output signal may have a predetermined format or profile, e.g. depending on the nature (e.g. shape or size) of the treatment site. The controller 126 may operate to deliver EM energy according to one or more delivery profiles. A user may be able to select a desired profile from a plurality of stored profiles, e.g. via a user interface 128 associated with the generator 102. For example, the generator may be configured in a similar manner to WO2012/076844, which discloses an electrosurgical apparatus in which RF and microwave energy are delivered to tissue down the same instrument, according to an energy delivery profile that can be set and automatically controlled based on feedback information.

The user interface 128 may include a display 130 for showing the selected profile and/or a stage or treatment or properties of tissue being treated.

Where the multiplexer 124 operates as a switch unit, generator 102 is capable of switching the energy supplied to the instrument between the three frequencies, according to a desired energy delivery profile. For example, the switch may first select the 14.5 GHz source, so that energy is delivered at 14.5 GHz, then switch to the 5.8 GHz source, so that energy is delivered at 5.8 GHz, and then switch to the 2.45 GHz source, so that energy is delivered at 2.45 GHz.

The multiplexer 124 may be a time-domain multiplexer. In this case, the multiplexer can rapidly alternate the energy supplied to the instrument between the three frequencies, according to a desired energy delivery profile. Alternatively, the multiplexer 124 may be a filter multiplexer, whereby it can supply the three frequencies to the instrument simultaneously, i.e. according to an energy delivery profile having a desired mixing ratio.

Hence, the energy delivery profile with which energy is delivered can be controlled by a combination of controlling an operational state of multiplexer 124 and the output of the separate microwave sources 122a, 122b, 122c.

In some embodiments, the generator 102 may include one or more reflected signal detectors arranged to measuring reflected power received back from the instrument 118, the radiating tip portion 204 of the instrument. By comparing the reflected signal with a signal delivered from the generator to the radiating tip portion, the generator can determine dielectric properties of the material (e.g. biological tissue) in contact with the instrument 118. The controller may be able to adjust operation of the multiplexer 124 and the separate microwave sources 122a, 122b, 122c based on the detected reflected power. The generator 102 may thus dynamically control energy delivery based on detected dielectric properties of the tissue being treated.

The apparatus 100 may further include a tuning network (not shown) between the signal generator 102 and the radiating tip portion 118, for helping to ensure a good impedance match with tissue as the tissue load changes. For example, a triple stub tuner may be used. Where a tuner is included between the generator 102 and the radiating tip portion 118, delivery of energy into tissue can be further improved by ensuring that the radiating tip portion has a good impedance match to the tissue in the middle of the tuning range.

Figure 2:
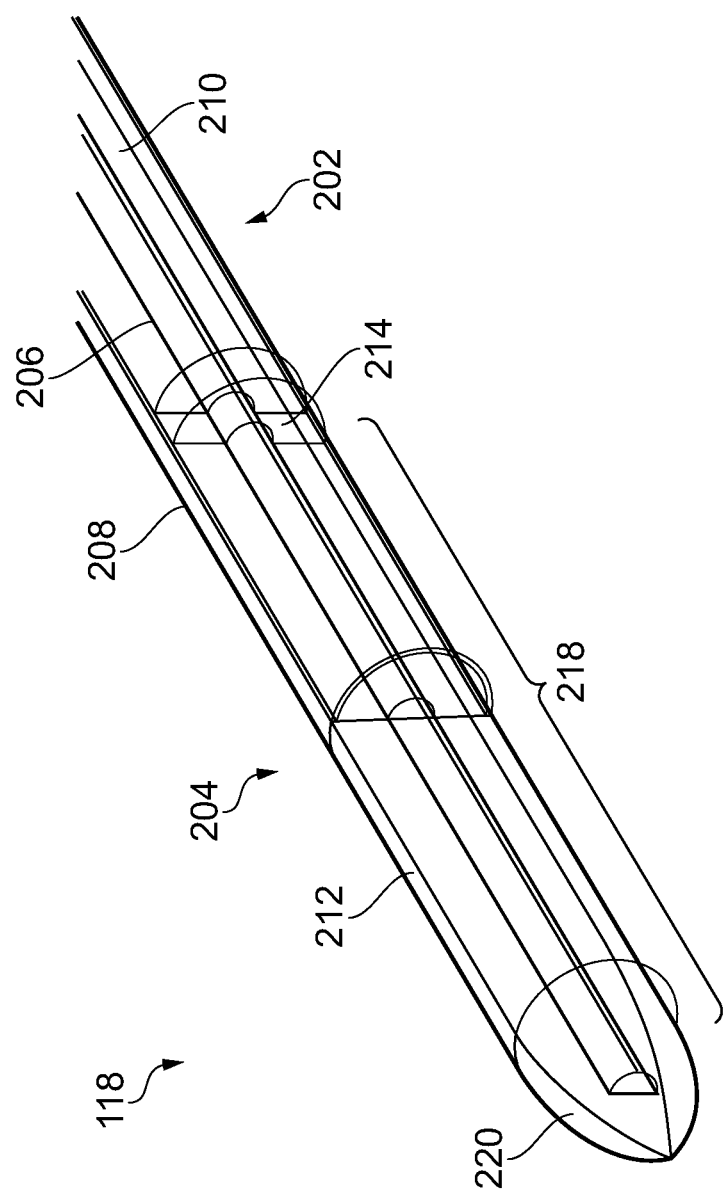
FIG. 2 is a cross-sectional view of the radiating tip portion of an electrosurgical instrument that is an embodiment of the present invention.

FIG. 2 shows a cross-section view through a distal portion of the electrosurgical instrument 118. The instrument 118 comprises a coaxial cable 202 (which may be the same as the coaxial cable 104 that is connected to the generator 102) and a radiating tip portion 204 located at and extending distally away from a distal end of the coaxial cable 202.

The coaxial cable 202 comprises an inner conductor 206, an outer conductor 208, and a first dielectric material 210 for electrically insulating the inner and outer conductors from each other. The outer conductor 208 may also be sheathed by a protective sleeve (not shown) to prevent electrical contact between the outer conductor and the tissue of a patient. The sheath is a biocompatible material, such as PTFE. A typical coaxial cable for use in the present invention has an impedance of 50Ω.

In order for the instrument to be suitable for insertion into a patient for surgical procedures, the outer diameter of the cable should be less than 5 mm. In embodiments in which the instrument is passed down the instrument channel of a bronchoscope 114, the outer diameter of the coaxial cable should be less than 1.5 mm, e.g. less than 1.2 mm. The coaxial cable has a length sufficient for it to be inserted into the body of a patient. Typically, it would have a length of 1 m or more, but is not limited to such a length.

In this application, unless stated otherwise, the length of a component refers to its dimension in the direction along (i.e. parallel to) the longitudinal axis of the coaxial cable.

The radiating tip portion 204 in this embodiment consists a second dielectric material 212 that is different from the first dielectric material 210. The second dielectric material 212 may be an elongate probe structure, e.g. having generally cylindrical shape. It may have a tapered, domed or pointed distal tip. A cylindrical shape is advantageous for use in surgical operations. The pointed shape of the second dielectric may help for percutaneous insertion into the body.

The second dielectric material 212 may abut a distal end of the first dielectric material 210. Alternatively, the second dielectric 212 may be separated from the first dielectric material by a collar 214 made from a third dielectric material that is different from both the first and second dielectric materials. The third dielectric in the present embodiment is a 1 mm air gap between the first and second dielectric materials. The air gap provides room for thermal expansion of constituent components of the instrument, without causing internal stresses on the cable or radiating tip portion which may otherwise cause damage to the instrument. Also, by having a gap of 1 mm, which is larger than the expected changes in the dimensions of the components of the coaxial cable, fluctuations in the size of the air gap are negligible, and resonances in the radiating tip portion are not particularly affected by such fluctuations.

The second dielectric 212 has an impedance that is selected to closely match the impedance of lung tissue at the frequencies of the microwave EM energy output by the separate microwave sources 122a, 122b, 122c. For example, the second dielectric may be made from Macor® ceramic, which is also rigid to further help with percutaneous insertion into the body. For the reasons already explained above, the Macor® ceramic is chosen as having an impedance between that of the coaxial cable, and that of the tissue into which the radiating tip portion is to deliver energy. This helps to reduce reflections at the radiating tip portion, and hence promote delivery of energy.

Outer conductor 208 extends beyond a distal end of the first dielectric material 210, so as to encase a proximal portion of the second dielectric material 212. The second dielectric 212 can be secured to the coaxial cable 202 in this manner, e.g. with or without additional fixing means, such as bonding or the like. The presence of the outer conductor 208 along the outer surface of the second dielectric material may affect the shape of a field emitted by the radiating tip portion. In particular, the emitted field may have a shape that is directed distally away from the distal end of the coaxial cable. The directional effect may be more pronounced for higher frequencies.

Beyond a distal end of the outer conductor 208, the second dielectric material 212 is exposed. The inner conductor 206 extends within the second dielectric material both beyond a distal end of the first dielectric material 210 and beyond a distal end of the outer conductor 208 to form a coaxial dipole antenna in the radiating tip portion. The inner conductor 206 may terminate within, e.g. just before the distal end of, the second dielectric material 212.

The second dielectric material 212 has a length selected to enable the radiating tip portion 204 to support resonance at 2.45 GHz, 5.8 GHz and 14.5 GHz when the radiating tip portion is inserted into body tissue, thereby maximising the energy delivered to body tissue (see below for the length used in the present example).

The length of second dielectric material 212 is selected in combination with its dielectric properties at the plurality of frequencies of microwave energy to be radiated so that it satisfies the equation:

$$L = \frac{n\lambda}{2},$$

where L is the length of the second dielectric material, n is a positive integer, and λ is the wavelength of energy in that propagates in the second dielectric material at the plurality of frequencies. The wavelength that propagates in the second dielectric material depends on frequency as follows:

$$\lambda = \frac{c}{f} \frac{1}{\sqrt{\mu_r(f)\varepsilon_r(f)}},$$

where c is the speed of light in vacuum, $\mu_r(f)$ is the frequency-dependent relative magnetic permeability of the radiating tip portion, and $\varepsilon_r(f)$ is the frequency-dependent relative dielectric permittivity of the second dielectric material. The frequency dependency of the dielectric permittivity and the magnetic permeability can be controlled to a certain extent by selecting a suitable dielectric material 212 for the radiating tip portion. Over the frequency ranges with which the present embodiment is concerned, the electric permittivity of Macor® ceramic is approximately constant, although frequency dependence of permittivity may play a part over larger frequency ranges. The dielectric loss (i.e. loss tangent) of the Macor® ceramic is also approximately constant over the frequency ranges with which the present embodiment is concerned.

Hence, the length of the second dielectric material 212 must be selected by taking into account the material into which the radiating tip portion is to be inserted, and the frequency-dependent magnetic and dielectric properties of the second dielectric material, such that it satisfies the following equation:

$$L = \frac{nc}{2f} \frac{1}{\sqrt{\mu_r(f)\varepsilon_r(f)}}$$

For Macor® ceramic inserted into lung tissue and supplied with energy at 2.45 GHz, 5.8 GHz, and 14.5 GHz, a second dielectric material 212 with a total axial length of 14.1 mm (of which the axial length of the parallel section 218 is 10 mm, and the axial length of the curved tip portion 220 is 4.1 mm, and where the outer conductor 208 encases the second dielectric 212 for the first 9 mm of the parallel section) satisfies this equation, such that the radiating tip portion 204 supports resonance at these frequencies.

For the purposes of the present application, the axial direction is the longitudinal direction of the coaxial cable.

It can be seen from the above equation that by choosing a second dielectric material 212 with a large dielectric constant (defined as the ratio of the relative permittivity of a material relative to permittivity in free space), the length of the radiating tip 204 portion can be small.

Figure 3:
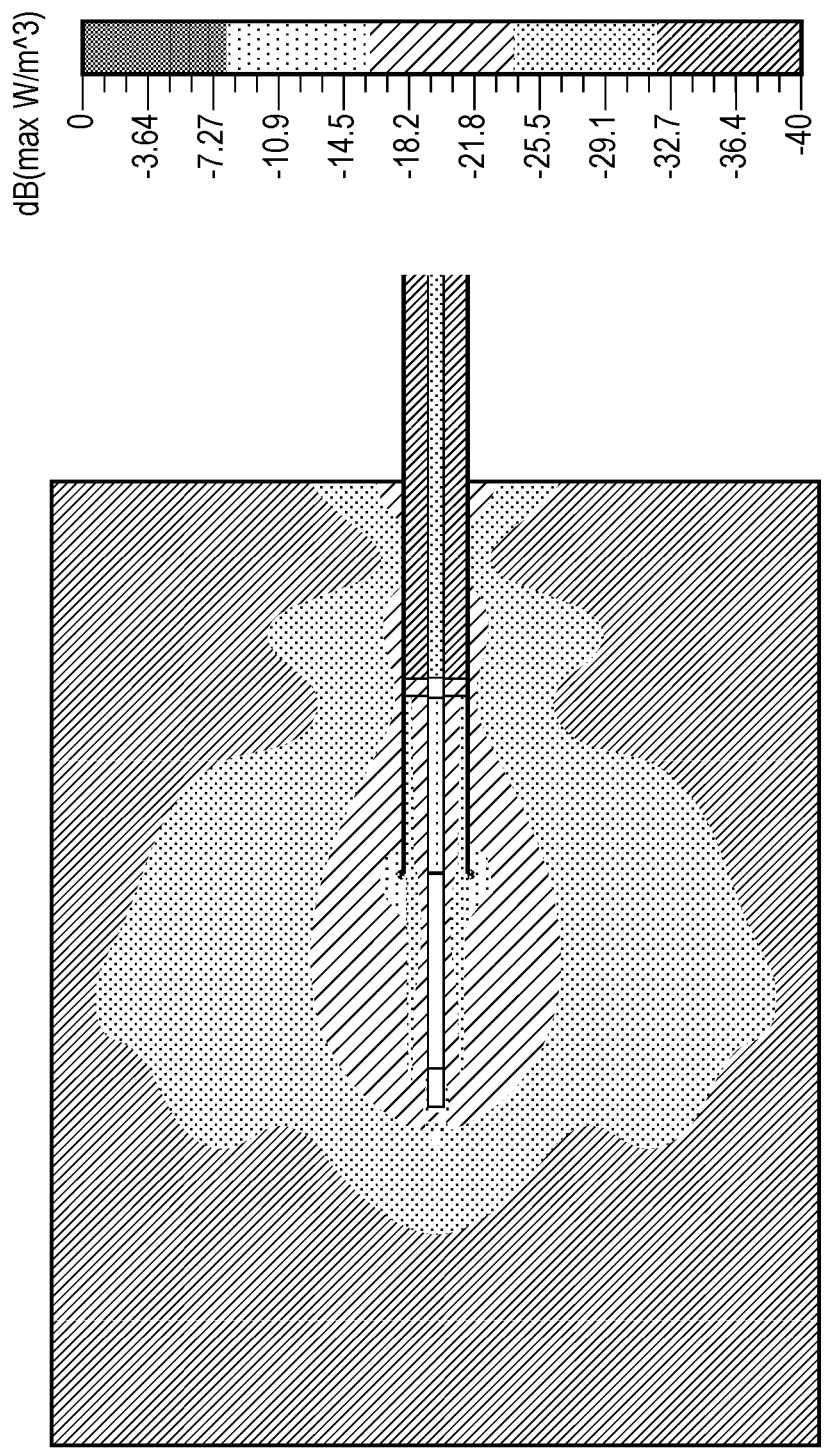
FIG. 3 is a simulated plot showing radiation power absorption density at 2.45 GHz for the instrument of FIG. 2 inserted into albumen.
Figure 4:
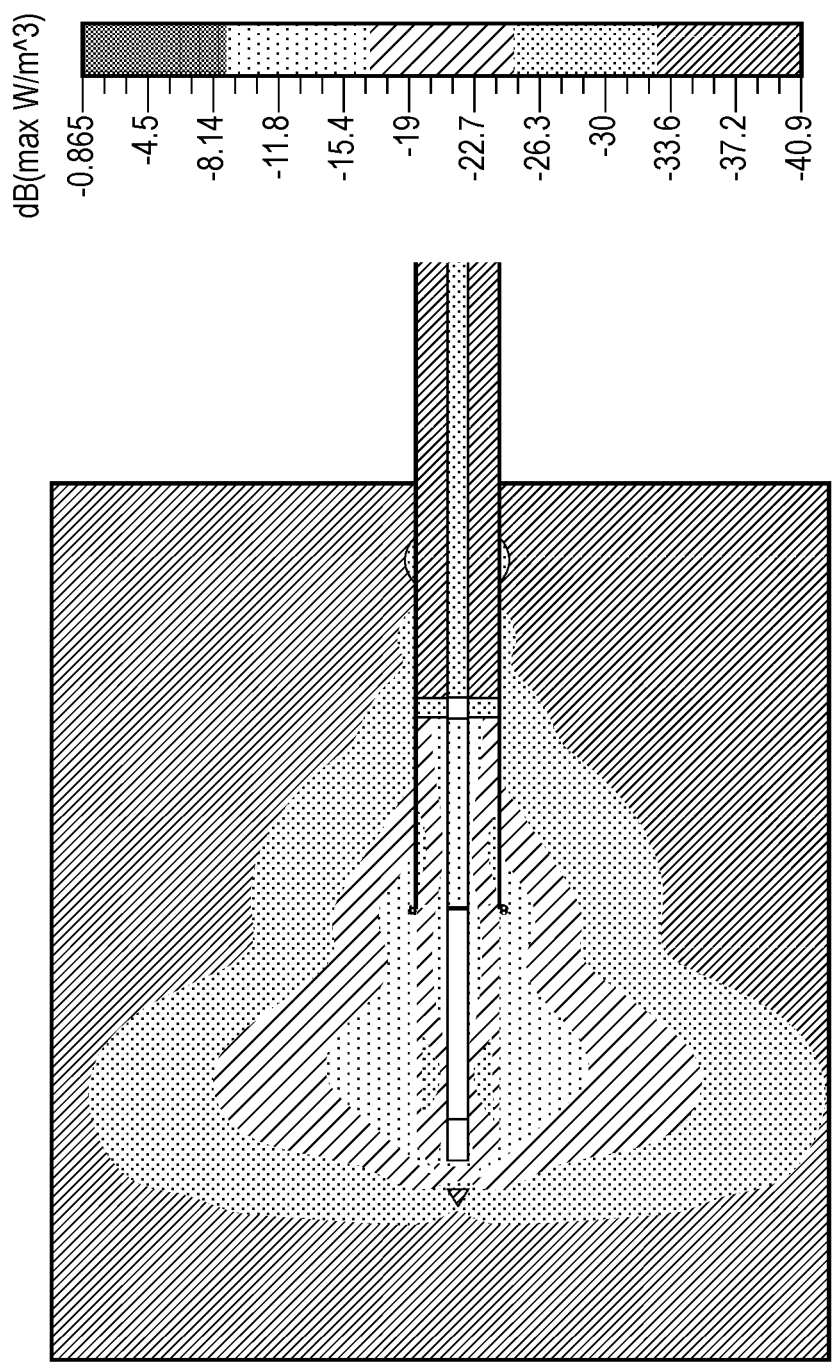
FIG. 4 is a simulated plot showing radiation power absorption density at 5.8 GHz for the instrument of FIG. 2 inserted into albumen.
Figure 5:
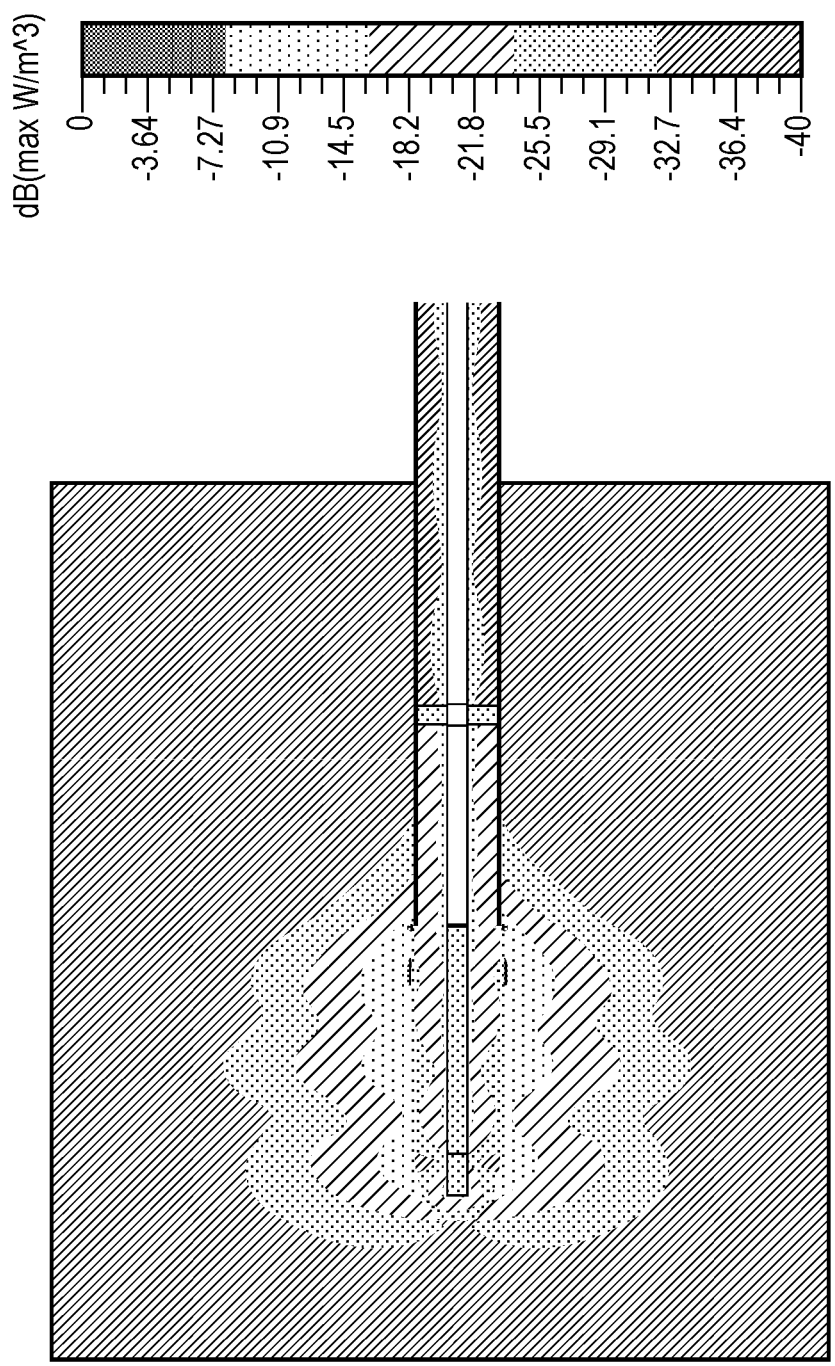
FIG. 5 is a simulated plot showing radiation power absorption density at 14.5 GHz for the instrument of FIG. 2 inserted into albumen.

FIGS. 3 to 5 are simulated plots showing radiation power absorption density at 2.45 GHz, 5.8 GHz and 14.5 GHz respectively, for radiating tip portion 204 when inserted into albumen. These simulations illustrate the different sizes and shapes of the fields emitted by the radiating tip portion at the various frequencies.

It is known that the depth of penetration of radiation depends on frequency. Table 1 below shows how ablation depth (referred to in the table as skin depth) varies for the frequencies of the separate microwave sources 122a, 122b, 122c.

TABLE 1 skin depth (in arbitrary units) at four different frequencies (GHz)

| Frequency (GHz) | Skin Depth (arb) |
|---|---|
| 2.45 | 22.1 |
| 5.80 | 7.39 |
| 14.5 | 1.96 |

FIG. 3 shows the simulated field shape for 2.45 GHz. The field extends radially away from the side surfaces of the exposed part of the second dielectric material. FIG. 4 shows the simulated field shape for 5.8 GHz. As expected, the radial size of the field is much smaller than for 2.45 GHz. However a distal portion of the field extends radially further than a proximal portion. FIG. 5 shows the simulated field shape for 14.5 GHz. Again, as expected, the radial size of the field is much smaller than for 2.45 GHz and 5.8 GHz. There is virtually no field expect in the immediate vicinity of the side surfaces of the exposed part of the second dielectric material.

The sizes and shapes of the fields discussed above can be usefully combined in certain delivery profiles.

For example, in a first profile, energy is supplied initial at 14.5 GHz only, in order to cause rapid heating of tissue close to the radiating tip portion. After a predetermined period of time has elapsed, i.e. after the tissue has been heated by the desired amount, the generator 102 then switches to supply energy at 5.8 GHz, i.e. to heat tissue slightly further afield. Advantageously, because the dielectric properties of the tissue adjacent to the radiating tip portion have changed through heating at 14.5 GHz, coupling of the EM energy to the tissue at 5.8 GHz is further improved, such that heating at 5.8 GHz occurs rapidly. After another predetermined period of time, i.e. after the tissue slightly further afield has been heated by a desired amount, the generator then switches again to supply energy at 2.45 GHz, in order to further increase the ablation depth. So, by supplying signals from the generator 102 according to such an energy delivery profile, deep ablation is achieved with reduced ablation time.

The time for which the energy is supplied at the three frequencies may be determined empirically, e.g. prior to treatment. Alternatively, the signal generator may determine an optimal time to switch frequency, e.g. when it is determined that the dielectric properties of the tissue at the radiating tip portion have changed by a requisite amount.

Alternating the energy supplied, or supplying the energy simultaneously or quasi-simultaneously using a filter/time-domain multiplexer (as appropriate) provides a similar effect, by enabling fast ablation of the tissue closest the radiating tip portion using 14.5 GHz energy, and ablating tissue further away from the radiating tip portion using the other two frequencies.

Figure 6:
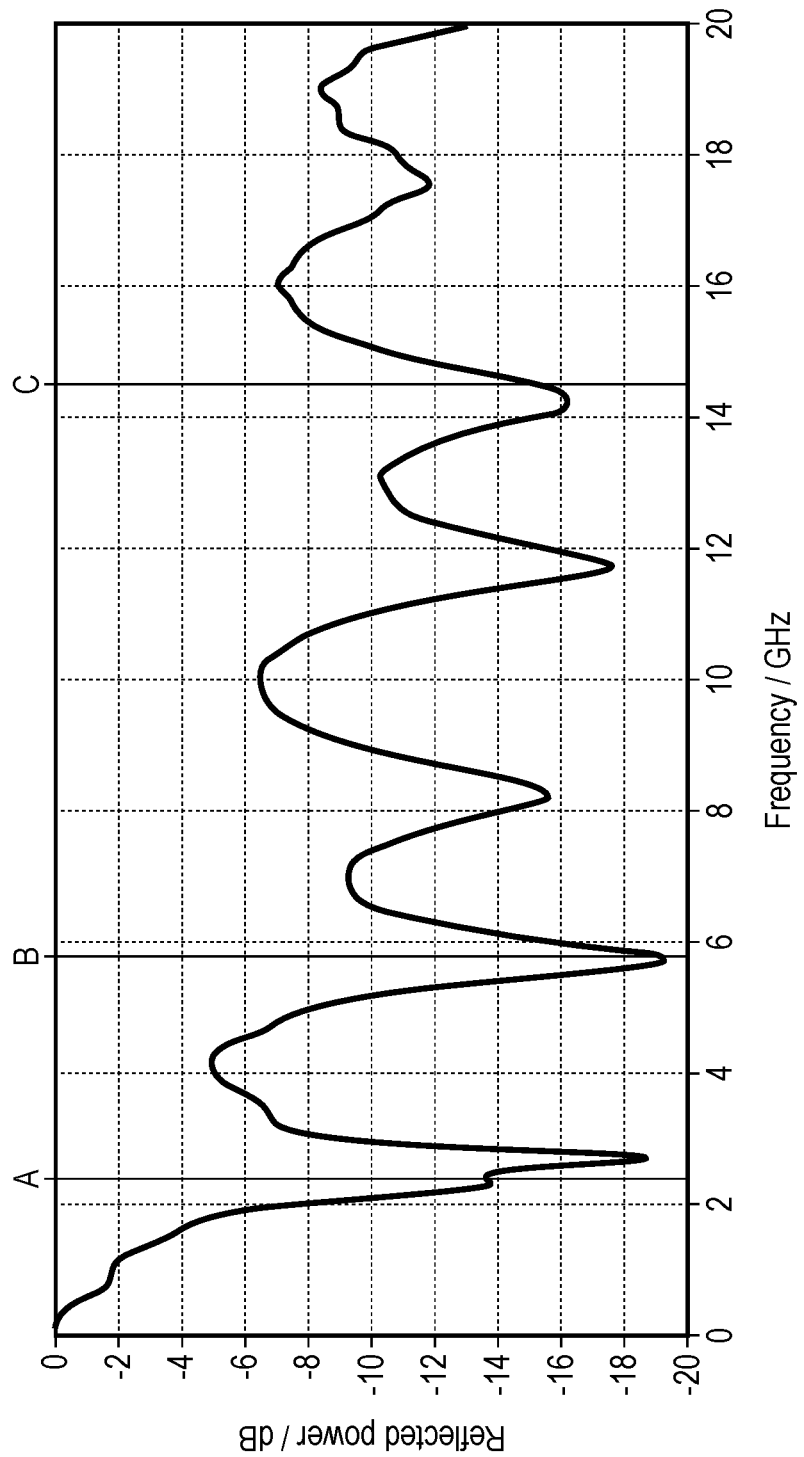
FIG. 6 is a graph showing a simulated $S_{1,1}$ resonance characteristic of the instrument of FIG. 2 over a range of frequencies.

FIG. 6 shows an $S_{1,1}$ plot of power reflected (in dB) from the radiating tip portion 204 of the instrument at frequencies up to 20 GHz, when inserted into albumen. The dips of the plot show points at which EM energy is stored in the tip (i.e. stored in the resonant standing wave at the tip), in preference to being reflected back along the coaxial cable to the generator. The dips therefore correspond to points of reduced reflected energy. Where reflected energy is reduced, energy is effectively delivered to tissue surrounding the radiating tip portion. Hence, the better the return loss, the better the delivery of energy. Labelled on the plot are: 2.45 GHz (A), 5.8 GHz (B), and 14.5 GHz (C). Hence, FIG. 6 shows that the instrument of FIG. 2 effectively couples energy to lung tissue at the three discussed frequencies. Moreover, at these three frequencies, the power reflected from the radiating tip portion 204 is −15 dB, or better. It may be noted that the instrument of FIG. 2 may also effectively deliver microwave energy having frequencies of 8.2 GHz and 11.7 GHz.

The invention claimed is:

1. An electrosurgical instrument for delivering microwave electromagnetic (EM) energy into biological tissue, the instrument comprising:
    a coaxial cable for conveying microwave EM energy, the coaxial cable having an inner conductor, an outer conductor, and a first dielectric material separating the inner conductor and the outer conductor; and
    a radiating tip portion disposed at a distal end of the coaxial cable to receive microwave EM energy from the coaxial cable, the radiating tip portion comprising a second dielectric material different from the first dielectric material,
        wherein the radiating tip portion has an electrical length selected in conjunction with its dielectric properties at three or more frequencies of microwave EM energy to support resonance at the three or more frequencies of microwave EM energy,
        wherein the radiating tip is configured to deliver the microwave EM energy at the three or more frequencies, in an alternating or simultaneous manner,
        wherein the three or more frequencies of microwave EM energy comprise a first frequency, a second frequency that is lower than the first frequency, and a third frequency that is lower than the first frequency and the second frequency, and
        wherein the second dielectric material has a length approximately equal to:
            2.5 wavelengths of the microwave EM energy at the first frequency in the second dielectric material;
            one wavelength of the microwave EM energy at the second frequency in the second dielectric material; and
            half a wavelength of the microwave EM energy at the third frequency in the second dielectric material.

2. An electrosurgical instrument according to claim 1, wherein the first frequency, second frequency and third frequency are 14.5 GHz, 5.8 GHz, and 2.45 GHz respectively.

3. An electrosurgical instrument according to claim 1, wherein a physical length L of the second dielectric material substantially satisfies $$L = n\lambda/2,$$

where n is a positive integer, and λ is a wavelength of microwave EM energy in the second dielectric material at each of the three of more frequencies of microwave EM energy.

4. An electrosurgical instrument according to claim 1, wherein the second dielectric material comprises an elongate probe extending distally away from the coaxial cable, the elongate probe having a cylindrical shape with a diameter equal to or less than a diameter of the coaxial cable.

5. An electrosurgical instrument according to claim 1, wherein the outer conductor extends beyond a distal end of the first dielectric material to enclose a proximal portion of the second dielectric material.

6. An electrosurgical instrument according to claim 1, wherein the inner conductor extends into the second dielectric material beyond a distal end of the outer conductor.

7. An electrosurgical instrument according to claim 1, wherein the second dielectric material has a lower impedance than the first dielectric material at each of the three of more frequencies of microwave EM energy.

8. An electrosurgical instrument according to claim 1, wherein the distal end of the radiating tip portion is tapered to a point.

9. An electrosurgical apparatus for delivering microwave electromagnetic (EM) energy into biological tissue, the apparatus comprising:
    a generator arranged to generate microwave EM energy at three or more different frequencies; and
    an electrosurgical instrument according to claim 1, wherein the coaxial cable has a proximal end connected to the generator to receive microwave EM energy therefrom.

10. An electrosurgical apparatus according to claim 9, wherein the generator comprises three or more separate microwave sources for generating microwave EM energy at a respective one of the three or more different frequencies.

11. An electrosurgical apparatus according to claim 10, wherein the generator comprises a multiplexer for receiving a signal from each of the three or more separate microwave sources, wherein the multiplexer is arranged to convey each signal to a common signal path that is connected to the coaxial cable.

12. An electrosurgical apparatus according to claim 11, wherein the multiplexer is operable as a switching unit for selecting a signal to be conveyed on the common signal path.

13. An electrosurgical apparatus according to claim 11, wherein the multiplexer is operable as a signal combiner to convey two or more of the signals on the common signal path in a simultaneous or quasi-simultaneous manner.

14. An electrosurgical apparatus according to claim 11, wherein the multiplexer is operable as a time-domain multiplexer.

15. An electrosurgical apparatus according to claim 11, wherein the multiplexer is operable as a filter multiplexer.

16. An electrosurgical apparatus according to claim 9 including a surgical scoping device having flexible instrument cord for non-invasive insertion to a treatment site, wherein the instrument cord includes an instrument channel, and wherein the electrosurgical instrument is dimensioned to be insertable within the instrument channel.

17. An electrosurgical apparatus according to claim 9, wherein the generator is operable to select an energy delivery profile for delivering the microwave EM energy at the three or more different frequencies.

18. An electrosurgical apparatus according to claim 17, wherein the generator is operable under the selected energy delivery profile to:
    deliver a first signal during a first ablation period, the first signal comprises microwave EM energy having predominantly the first frequency;
    deliver a second signal during a second ablation period, the second signal comprises microwave EM energy having predominantly the second frequency; and
    deliver a third signal during a third ablation period, the third signal comprises microwave EM energy having predominantly the third frequency.

19. An electrosurgical apparatus according to claim 18, wherein the second frequency is less than half the first frequency.

20. An electrosurgical apparatus according to claim 18, wherein the third frequency less than half the second frequency.

21. An electrosurgical apparatus according to claim 18, wherein the first frequency is 14.5 GHz, the second frequency is 5.8 GHz, and the third frequency is 2.45 GHz.

22. An electrosurgical apparatus according to claim 18, wherein the generator includes a detector arranged to detect reflected power received back from the coaxial cable, and wherein the generator is arranged to switch from one ablation period to the next ablation period based on the detected reflected power.

* * * * *